Figure 1:
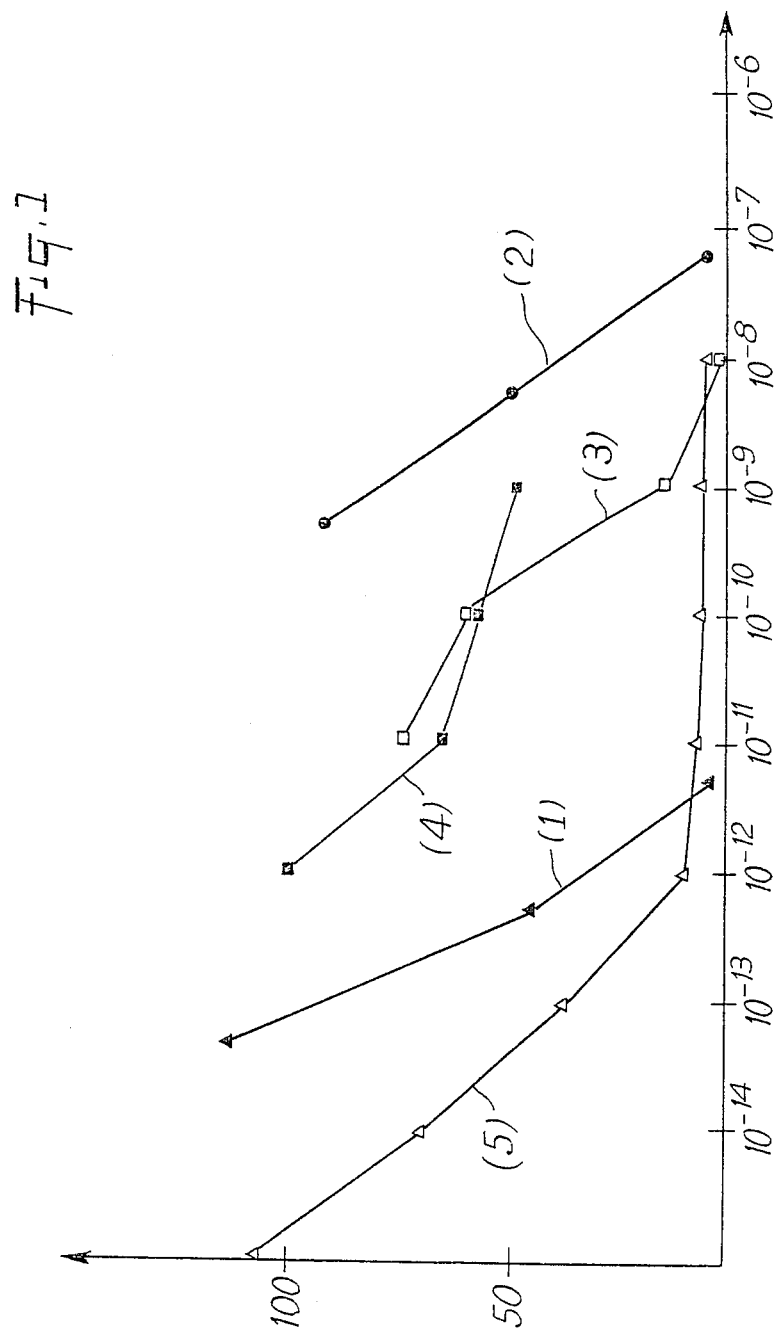

United States Patent [19]

Jansen et al.

[11] Patent Number: 4,762,707

[45] Date of Patent: Aug. 9, 1988

[54] NEW CONJUGATES ASSOCIATING, BY COVALENT BOND, AN ENZYME WITH AN ANTIBODY, AND MEDICINAL ASSOCIATIONS USING THE SAID CONJUGATES

[75] Inventors: Franz Jansen, St. Mathieu De Treviers; Pierre Gros, Montpellier, both of France

[73] Assignee: Sanofi (Societe Anonyme), Paris, France

[21] Appl. No.: 736,334

[22] Filed: May 21, 1985

Related U.S. Application Data

[63] Continuation of Ser. No. 475,127, Mar. 14, 1983, abandoned.

[30] Foreign Application Priority Data

Mar. 17, 1982 [FR] France ................................ 82 04547

[51] Int. Cl.⁴ .................. A61K 39/395; A61K 39/44; A61K 37/48; C12N 11/02
[52] U.S. Cl. .................................... 424/85; 424/94.3; 455/177
[58] Field of Search ...................... 435/7, 177; 424/85, 424/94

[56] References Cited

U.S. PATENT DOCUMENTS

| | | | |
|---|---|---|---|
| 4,218,539 | 8/1980 | Weltman | 435/7 |
| 4,232,119 | 11/1980 | Carlsson et al. | 435/7 |
| 4,340,535 | 7/1982 | Voisin et al. | 424/85 |
| 4,414,148 | 11/1983 | Jansen et al. | 424/85 |
| 4,643,895 | 2/1987 | Casellas et al. | 424/85 |

OTHER PUBLICATIONS

King, T. et al., J. Immunol, Methods, vol. 28, pp. 201–210, 1979.
Chemical Abstracts, vol. 70, Abst. No. 1046235, 1969.
Biological Abstracts, vol. 71, Abst. No. 31289, 1980.
Chemical Abstracts, vol. 96, Abst. No. 329792, 1982.
Comprehensive Biochemistry, Florkin, vol. 13, 3d Ed., Enzyme Nomenclature, Elsevier Scientific, 1973.

*Primary Examiner*—Blondel Hazel
*Attorney, Agent, or Firm*—Bacon & Thomas

[57] ABSTRACT

The present invention relates to new immunoenzymic conjugates resulting from a chemical coupling, by covalent bond, of an antibody or a fragment of antibody, which has retained the capacity of recognizing the selected antigen, with an enzyme capable of producing ammonium ions from natural substrates which are well tolerated in higher animal organisms.

The invention also relates to a process for the preparation of these conjugates and the medicinal associations of said conjugates with an immunotoxin.

11 Claims, 2 Drawing Sheets

NEW CONJUGATES ASSOCIATING, BY COVALENT BOND, AN ENZYME WITH AN ANTIBODY, AND MEDICINAL ASSOCIATIONS USING THE SAID CONJUGATES

This application is a continuation of application Ser. No. 475,127, filed Mar. 14, 1983.

The present invention relates to:

new products which are conjugates associating, by covalent bond, an enzyme with an antibody or fragments of antibodies, and to the medicinal associations, with an immunotoxin, containing said novel products.

The new products according to the invention are therefore conjugates obtained by covalent bond of a specific enzyme with antibodies or fragments of antibodies directed against an antigen carried by target cells.

Such compounds are designated hereinafter as immunoenzymic conjugates.

These immunoenzymic conjugates are artificial mixed molecules in which the enzyme is associated by covalent bond with an antibody directed against an antigen carried by the target-cells.

The enzymes used are known compounds. The antibody used will be either of a polyclonal nature if it is obtained by a conventional immunization conducted on an animal, or of a monoclonal nature if it is produced by a clone of hybrid cells obtained by fusion between lymphocytes and myeloma cells. Said antibody can be used either as whole molecules of immunoglobulin which have the ability to recognize the selected antigen, or as any fragment of these immunoglobulin molecules which has retained the ability to recognize the selected antigen and in particular fragments known as $F(ab')_2$, Fab and Fab'.

The chemical coupling of the antibody (or fragment of antibody) with the enzyme can be achieved by many methods, provided that the selected method:

preserves the respective biological activities of the two components of the conjugate: antibody and enzyme, secures for the process a satisfactory reproducibility and a good coupling yield, enables to control the value of the enzyme/antibody ratio in the resulting conjugate, and gives a stable and water-soluble product.

Amongst the methods fulfilling these requirements, the most expedient ones are those using one or more thiol functions to obtain the bond between the two proteins. Said thiol functions can indifferently belong to either one of the proteins to be coupled, or else be artificially introduced on one or the other protein not naturally containing thiol.

If one or more thiol groups are thus to be artificially introduced on one of the proteins, this can be done by the action on said protein of S-acetylmercaptosuccinic anhydride, capable of acylating some of the amino functions of the protein. The thiol function can thereafter be released by elimination of the protecting acetyl radical, by action of hydroxylamine, as described in "ARCHIVES OF BIOCHEMISTRY AND BIOPHYSICS 119, 41–49, (1967)". A dialysis enables to eliminate any excess of reagents as well as the reaction products of low molecular mass. Other methods described in the literature can also be used to introduce thiol functions in one of the proteins to be coupled.

According to the invention, that of the two proteins which alone possesses one or more thiol functions is reacted with the other protein in which has been introduced beforehand one or more functions capable of reacting with thiols, in aqueous medium, of pH between 5 and 9 and at a temperature not exceeding 30° C., to give a stable and specific covalent bond. Said covalent bond will be in particular, either a disulfide bond, or a thioether bond. $P_1$ is used hereinafter to designate that of the two proteins which carries the thiol function or functions and $P_2$ is used to designate the other protein to be coupled.

(1) Case of the disulfide bond:

The preparation of the conjugate can then be represented by the following scheme:

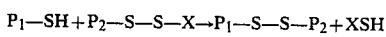

$$P_1-SH + P_2-S-S-X \rightarrow P_1-S-S-P_2 + XSH$$

wherein:

—S—S—X designates an activated mixed disulfide group of which X is the activator radical.

The protein $P_2$ substituted by an activated sulfur atom is obtained from the protein $P_2$ itself, by substitution with the aid of a reagent, itself carrier of an activated sulfur atom according to the scheme:

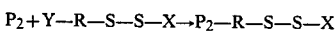

$$P_2 + Y-R-S-S-X \rightarrow P_2-R-S-S-X$$

wherein:

$R_2$ is the protein to be substituted

Y represents a function allowing covalent fixation of the reagent on the protein.

R designates a group which may simultaneously carry the substituents Y and —S—S—X X designates the activator radical.

The functional group Y is a function capable of bonding covalently with any one of the functions carried by the side chains of the aminoacids constituting the protein to be substituted. From among these, the terminal amino functions of the lysyl radicals contained in the protein are particularly indicated. In this case, Y may represent, in particular:

a carboxylic group which may bond with the amino functions of the protein in the presence of a coupling agent such as a carbodiimide and in particular a water-soluble derivative such as 1-ethyl 3-(3-diethyl-amino propyl)carbodiimide, a chloride of carboxylic acid which is capable of reacting directly with the amino functions to acylate them, a so-called "activated" ester such as an ester of ortho- or para-, nitro- or dinitro-phenyl or an ester of N-hydroxy succinimide which reacts directly with the amino functions to acylate them, an internal anhydride of a carboxylic diacid such as for example succinic anhydride which react spontaneously with the amine functions to create amide bonds, an imidoester group

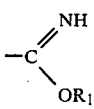

where $R_1$ is an alkyl group reacting with the amino groups of the protein according to the reaction

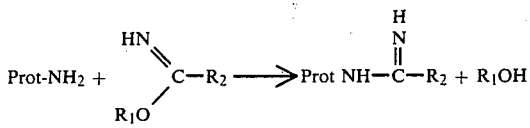

The radical —S—S—X designates an activated mixed disulfide capable of reacting with a free thiol radical. In particular in this mixed disulfide, X may designate at 2-pyridyl or 4-pyridyl group possibly substituted by one or more alkyl, halogen, carboxylic radicals. X may also designate a phenyl group preferably substituted by one or more nitro- or carboxylic groups. X may further represent an alkoxycarbonyl group such as the methoxycarbonyl group.

The radical R designates any radical capable of simultaneously carrying the substituents Y and S—S—X. It must be selected so as not to comprise any functions capable of interfering in the course of the subsequent reactions with the reagents used and the synthesized products. In particular, the group R may be a group —$(CH_2)_n$ with n included between 1 and 10, or a group:

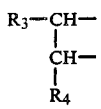

in which $R_4$ designates hydrogen or an alkyl group having from 1 to 8 atoms of carbon and $R_3$ designates a substituent which is inert with respect to the reagents used subsequently such as a carbamate group

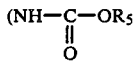

where $R_5$ designates a straight or branched alkyl group having from 1 to 5 atoms of carbon and particularly the tertiobutyl group.

The reaction of the compound Y—R—S—S—X with the protein $P_2$ is carried out in homogeneous liquid phase, most often in water or a buffer solution. When the solubility of the reagents requires this, it is possible to add to the reaction medium up to 20% by volume of a water-miscible organic solvent such as an alcohol and particularly tertiary butanol.

The reaction is carried out at ambient temperature for a period of time varying from a few hours to 24 hours. After which a dialysis makes it possible to eliminate the products of low molecular mass and, in particular, the excesses of reagents. This process makes it possible to introduce a number of substituent groups per mole of protein of normally between 1 and 15.

By using such compounds, the coupling with Protein $P_1$ is effected by bringing together in aqueous solution the two proteins at a temperature not exceeding 30° C. for a period of time varying from a few hours to a day. The solution obtained is dialysed to eliminate the products of low molecular mass, then the conjugate may be purified by various known methods.

(2) Case of the thioether bond:

The preparation of the conjugate consists then in reacting $P_1$—SH with the protein $P_2$ on which a maleimide group has been introduced beforehand.

The reaction is then represented by the scheme:

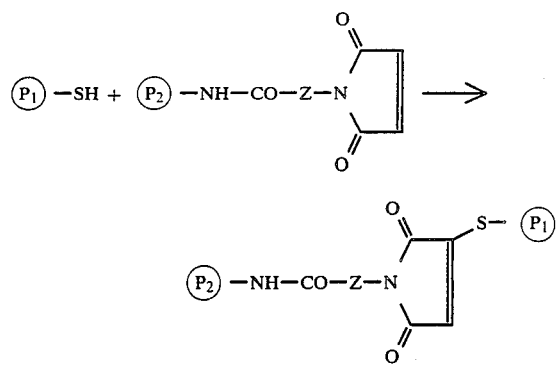

wherein:

Z is an aliphatic or aromatic spacing structure with 1 to 10 carbon atoms.

The protein $P_2$ substituted the maleimide is obtained from the protein $P_2$ itself, by substitution of the amino functions of the protein with the aid of a reagent itself carrier of the maleimide group, according to the scheme:

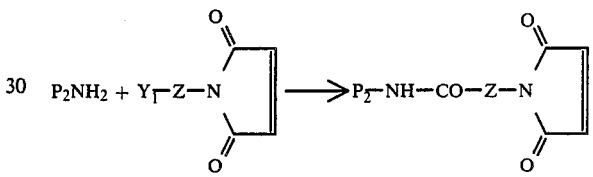

wherein $Y_1$ is:

either a carboxylic group, the reaction being then effected after activation of the carboxylic function in the presence of a coupling agent such as a carbodiimide and in particular a water-soluble derivative such as 1-ethyl 3-(3-dimethylamino propyl)carbodiimide, or a so-called "activated" ester such as an ester of ortho-, or para-, nitro- or dinitro-phenyl, or else an ester of N-hydroxy succinimide which reacts spontaneously with the amino functions to acylate them.

The preparation of such reagents is in particular described in Helvetical Chimica Acta 58, 5"1-541, (1975). Other reagents of the same class are available on the market.

The reaction of the compound

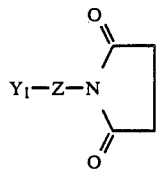

with the protein $P_2$ is carried out in homogeneous liquid phase, most often in water or a buffer solution. When the solubility of the reagents requires this, it is possible to add to the reaction medium up to 20% by volume of a water-miscible organic solvent such as an alcohol and particularly tertiary butanol.

The reaction is carried out at ambient temperature for a period of time varying from a few hours to 24 hours. After which a dialysis makes it possible to eliminate the products of low molecular mass and, in particular, the excesses of reagents. This process makes it possible to introduce a number of substituent groups per mole of protein of normally between 1 and 15.

By using such compounds, the coupling with the protein $P_1$ is effected by bringing together in aqueous solution the two proteins at a temperature not exceeding 30° C. for a period of time varying from a few hours to a day. The solution obtained is dialysed to eliminate the products of low molecular mass, then the conjugate may be purified by various methods.

Such immunoenzymic conjugates can be produced with any enzyme. However, for the pharmaceutical use for which they are destined and which is described hereinafter, the preferred enzymes are those capable of releasing ions of ammonium from natural substrates well tolerated in senior animal organisms.

According to the international classification such as this is presented for example in Volume 13 of the "Comprehensive Biochemistry", 3rd publication (1973), by M. Florkin and E. H. Stortz (Elsevier), the pharmaceutically suitable enzymes to be used in the invention are mainly found:

in group 1 (oxydoreductases) and in particular in sub-group 1-4 containing the aminoacids-dehydrogenases and the amino-oxidases;

in group 3 (hydrolases) and in particular in sub-group 3-5 containing the enzymes hydrolyzing amides, amidines, and other bonds C—N (excluding the peptidic bonds):

in group 4 (lyases) and in particular in sub-groups 4-2 and 4-3 containing the enzymes catalyzing degradation reactions with formation of non-saturated compounds.

The following is a list of the enzymes considered as expedient to produce the immunoenzymic conjugates according to the invention. In each case is also indicated the code used to designate these enzymes in the international nomenclature.

1-4-1-1: alanine dehydrogenase
1-4-1-3: glutamate dehydrogenase NAD (P)+
1-4-1-5: L-amino-acids dehydrogenase
1-4-3-2: L-amino-acids oxydase
3-5-1-1: asparaginase
3-5-1-2: glutaminase
3-5-1-4: amidase
3-5-1-5: urease
3-5-3-6: arginine deaminase
3-5-4-4: adenosine deaminase
3-5-4-6: adenosine monophosphate deaminase
3-5-4-21: creatinine deaminase
4-2-1-13: L-serine dehydratase
4-2-1-16: L-theonine dehydratase
4-3-1-1: aspartate-ammonia-lyase (or aspartase)
4-3-1-3: histidine-ammonia-lyase (or histidase)
4-3-1-5: phenylalanine-ammonia-lyase.

A second aspect of the invention concerns the use in human therapeutics of these immunoenzymic conjugates.

In earlier French patent applications, Nos. 78 27 838, 79 24 655, (these applications correspond to U.S. Pat. No. 4,340,535) 81 07 596 (which corresponds to U.S. Pat. No. 4,414,148) and 81 21 836, (which corresponds to U.S. Pat. No. 4,643,895) Applicants described the preparation of so-called conjugate anti-cancer products obtained by coupling, by covalent bond, the chain A or ricin with antibodies or fragments of antibodies directed against an antigen carried by the cell to be destroyed. The products of this type are designated in the present application under the generic name of immunotoxins.

French patent application No. 81 21 836 (which corresponds to U.S. Pat. No. 4,643,898) also describes the properties of ammonium ions (in the form of any one of their salts and in particular chloride) to potentiate efficiently the cytotoxic action of these immunotoxins.

The property of the ammonium salts to potentialize the selective cytotoxic activity of the immunotoxins presents many advantages in two types of cases:

(a) Every time an immunotoxin is used as a selective cytotoxic agent in vitro to destroy the target-cells In therapeutics, this particular case is met for example when the immunotoxin is used as a cytotoxic agent to treat the bone marrow of leukaemic sufferers in whom the so-treated bone marrow will be subsequently transplanted, as described in Applicants' French patent application No. 81 21 826.

(b) When the immunotoxin is used in vivo in human therapeutics whenever it is possible to administer an ammonium salt to the patient either before, or simultaneously or subsequently to the immunotoxin, to ensure the potentialization of the effect of the immunotoxin such as described in the aforementioned patent application.

In this last case however, wherein the immunotoxin is used in vivo, the use also in vivo of an ammonium salt in order to take advantage of the potentializing effect has certain limitations which are inherent to the actual toxicity of the ammonium ions and to the fact that it is relatively difficult to keep for long periods of time a sufficient concentration of ammonium ions in the biological liquid of the patient.

The works conducted by the Applicants have permitted to reduce to a considerable extent the limitations related to the use of ammonium ions whilst preserving the advantages of the potentialization of the cytotoxic activity and of the kinetics of action of the immunotoxins by these ions. These works have indeed shown that the potentializing and accelerator effect, obtained by adding to the immunotoxins an ammonium salt in suitable concentration, could likewise be obtained if the ammonium ions were produced in the immediate environment of the target-cells by an enzymic reaction from a non-toxic substrate naturally present or artificially introduced in the environment of these cells.

These works have also shown that this result is obtained particularly efficiently when the enzyme which catalyzes the reaction producing the ammonium ions is coupled with an antibody (or fragment of antibody) capable of recognizing an antigen present on the surface of the target-cells.

This method of proceeding presents considerable advantages, some of which are given hereunder:

(a) The enzyme used is thus concentrated on the membrane of the target-cells because of the affinity of the antibody (or fragment of antibody) for an antigen present on said membrane. As a result, the release of $NH_4^+$ ions as products from the enzymic reaction will only occur in the immediate vicinity of the membrane of the target-cells, this reducing the risk related to the general toxicity of ammonium ions, whilst aiding the interaction of these ions with the target-cells, said interaction being necessary for the potentialization to occur.

(b) The enzymic reaction producing the $NH_4^+$ ions in continuous manner as long as the substrate is present, and this substrate being selected because being non-toxic, this process allows great flexibility of use of the potentializing mechanism. Indeed:

If the substrate is endogenous and has the adequate concentration, the potentializing immunoenzymic conjugate can be administered before or simultaneously or subsequently to the administration of the immunotoxin depending on the optimum conditions to be defined for each patient.

If, moreover, the enzyme is selected so that its substrate does not exist in the blood, and the extracellular liquid in a high enough concentration, and that said substrate therefore also has to be administered to the patient, the adapatability of use of the drug then appears, to its maximum since it becomes possible to adjust freely and independently, the administration time, its duration and the quantity of each of the three components administered, namely the immunotoxin, the immunoenzymic conjugate and the substrate, in relation to the optimum conditions defined for the treatment of each patient.

(c) In the conditions indicated hereinabove, at least two effector substances necessary to the expected result will be selectively directed on the target-cells:

on the one hand, the chain A of ricin which is the cytotoxic effector contained in the so-called immunotoxin conjugate;

on the other hand, the enzyme which is an essential component of the potentializing system, and is contained in the immunoenzymic conjugate.

These effector substances are in all cases coupled, with a view to be directed and selectively fixed on the target-cells, with antibodies (or fragments of antibodies) recognizing antigens present on the surface of the target-cells. If the antibody used is capable of recognizing an antigen which is strictly specific to the cell population to be destroyed, then the same antibody can also be used for the coupling with the different effectors. But in the more general cases, it is advisable to select different antibodies recognizing different antigens but all of them carried by the target-cells. Then, even if each one is not strictly specific to the target-cells, it is quite improbable that the two antigens selected will both be present on non-target-cells and then we have an extremely powerful means to further increase the specific character of the citotoxicity of the immunotoxins.

The following examples are given to illustrate nonrestrictively the invention.

EXAMPLE 1

Immunoenzymic conjugate obtained by reacting an anti-dinitrophenyl antibody substituted by an activated disulfide group with a urease of vegetable origin.

(a) Anti-dinitrophenyl antibody (Anti-DNP)

This antibody is a monoclonal antibody which has been purified by the conventional techniques from abdominal dropsy fluid from mice of the Balb/C strain in which has been transplanted the hybridoma $F_9$.

Said hybridoma has itself been obtained by fusion between splenic cells of mice of Balb/C strain immunized with bovine γ-globulin on which have been priorly fixed 20 DNP radicals per mole with cells of the murin NS 1 myeloma stock, and isolated by cloning, according to the conventional techniques. The resulting antibody is an immunoglobulin of class G and of isotype 2b whose constant of affinity (measured for the ligand ε-DNP-lysin) is $1{,}8\times10^{8}M^{-1}$.

(b) Activated anti-DNP antibody

This product was obtained from the preceding antibody, according to a technique similar to those described in earlier applications No. 78 27 838 with Addition 79 24 655, and Nos. 81 07 596 and 81 21 836. The 20 mg of anti-DNP antibody thus obtained contain 1.2 activator group per mole.

(c) Urease

The enzyme used is the urease of SIGMA origin (Type VII, reference U 0376), assayed at 170 units per mg. One unit is the quantity of enzyme permitting to release 1 micromole of $NH_4^+$ per minute at 20° C., and with a pH of 7.0, from urea.

Said enzyme naturally possesses 27 thiol groups per mole of molecular weight 480,000. Said thiol groups, assayable by the ELLMAN method, are not all necessary to the enzymic activity. Some may therefore be used for the coupling with the activated antibody.

(d) Coupling of the antibody with the enzyme 5 mg of urease are dissolved in 0.625 ml of solution of activated antibody at 7.2 mg/ml in the phosphate buffer 0.125M, pH 7.0, i.e. 4.5 mg of activated antibody. Incubation is allowed to go on at 25° C. for 14 hours.

The reaction mixture is chromatographed over a Sepharose 6B (Pharmacia) gel column balanced in a PBS buffer (phosphate 10 mM, sodium chloride 140 mM, pH 7.4). The elution is controlled by measuring the optical density at 280 nm and by measuring the urease activity according to the SUMMER method (Methods in Enzymology Vol. II, page 378, S. B. Colowick and N. O. Kaplan Ed., Academic Press, 1955).

The fractions containing the strongest urease activities are regrouped, giving 8 ml of solution of conjugate at 6.5 units/ml.

If an aliquot fraction of said solution is absorbed on a column of bovine albumin serum substituted by six DNP radicals per mole and made insoluble on a matrix of Sepharose 4 B previously activated by cyanogen bromide, it is found that the urease activity remains entirely absorbed on the column. This also shows that the antibody present in the conjugate has retained its capacity to recognize the DNP hapten and that the the urease is really coupled with said antibody.

EXAMPLE 2

Potentialization of Anti T65 immunotoxin

The conjugate according to the invention obtained as indicated hereinabove, has been studied with regard to its biological properties and more particularly its capacity to potentialize the activity of the anti T65 immunotoxin in an appropriate cellular model.

Said model is constituted by cells of the lymphoblastoid human CEM cellular stock, which naturally carry the antigen T65. Said antigen, against which is directed the immunotoxin used, constitutes the first target antigen of the model. It is also possible to mark these cells with trinitrophenyl hapten (TNP) according to the method described in earlier application No. 78 27 828. Said hapten is perfectly well recognized by the anti-DNP antibody contained in the tested immunoenzymic conjugate and as such constitutes the second target-antigen of the model. It has been proved that the marking of cells with TNP hapten does not alter the viability of the cells and does not interfere with the fixation on these cells of the anti-T65 immunotoxin.

The basic property of these immunotoxins being to inhibit the proteosynthesis of the target-cells, the test used consists in measuring the effect of the tested substances on the incorporation of $^{14}C$-leucine in the cancerous cells in culture.

This measurement is effected according to a technique adapted from the technique described in the Journal of Biological Chemistry, 1974, 249, (ii), 3557-62 using the $^{14}$C-leucine tracer for determining the rate of proteosynthesis. The determination of the incorporated radioactivity is here effected on the whole cells isolated by filtration.

From these determinations, the dose/effect curves can be plotted, the x-axis showing the molar concentration of chain A of the substances studied and the y-axis the incorporation of $^{14}$C-leucine expressed as percentage of the incorporation of the control cells in the absence of any substance affecting the protein synthesis.

The drawings are dose/effect curves representing the experiments which were conducted for each substance studied. The concentration which inhibits 50% of the incorporation of $^{14}$C-leucine or "inhibitory concentration 50" (IC 50).

For each substance studied, the concentration which inhibits 50% of the incorporation of $^{14}$C-leucine or "inhibitory concentration 50" (IC 50) may thus be determined.

The different tests in this experiment were conducted as follows. The corresponding experimental results are presented in FIG. 1.

(a) CEM cells are incubated for 18 hours at 37° C. in the presence of known concentrations of ricin or of isolated chain A, used as reference substances, after which the radioactive tracer is incorporated to the cells. The resulting IC 50 are respectively $4 \times 10^{-12}$M and $4,5 \times 10^{-8}$M for ricin and the chain A. It has also been found that these values are indistinguishable from those obtained on CEM cells marked with TNP hapten. (Curve 1, ricin on CEM and Curve 2, chain A ricin on CEM).

(b) CEM cells marked by TNP are incubated for 18 hours at 37° C. in the presence of an immunotoxin of anti-DNP specificity, obtained as indicated in earlier application No. 78 27 838 and addition No. 79 24 655 and then subjected to the incorporation of the radioactive tracer. The shape of the cytotoxicity curve obtained and the value of the IC 50($1,5 \times 10^{-9}$M) show that these cells are normally sensitive to the cytotoxic effect of anti-DNP immunotoxin, thereby proving that these cells are correctly marked by TNP (Curve 3).

(c) CEM cells marked by TNP are first incubated for 1 hour at 4° C. in the presence of non-conjugated urease in the proportion of 5 U/ml, then they are washed, incubated for 18 hours at 37° C. in the presence of the anti-T65 immunotoxin and urea 5M and finally subjected to the incorporation of the radioactive tracer. The IC 50 obtained is $5 \times 10^{-9}$M. This value is identical to that obtained by using CEM cells not marked with TNP in the same conditions, without the treatment by urease and without urea in the incubation medium after washing the urease. This test shows that the incubation in the presence of non-conjugated urease entails no bonding of the urease to the cells and as a result, no potentialization of the effect of the anti T65 immunotoxin (Curve 4).

(d) CEM cells marked by TNP are first incubated for 1 hour at 4° C. in the presence of the immunoenzymic conjugate described hereinabove, used at a concentration of 6.5 U/ml. It was found on the other hand that this conjugate, when used in these conditions, has no inherent cytotoxicity on the cells used. These cells are thereafter washed to eliminate all conjugates which would not be fixed, then they are incubated for 18 hours at 37° C. in the presence of anti T65 immunotoxin and urea 5M. They are finally subjected to the incorporation of the radioactive tracer. The IC 50 obtained is $3,5 \times 10^{-13}$M (Curve 5).

This result shows that the potentializing effect of the immunoenzymic conjugate increases by about 14,000 times the cytotoxic activity of the immunotoxins on the target cells. This test proves that this potentializing effect implies the fixation of the immunoenzymic conjugate on the antigen corresponding to its immunologic specificity. Said fixation withstands the washing of the cells and leaves on their surface some enzymically active urease which produces $NH_4^+$ ions from the urea present in the incubation medium with the immunotoxin, this entailing the well known potentializing effect of the $NH_4^+$ ions. The potentializing effect obtained is quite similar to that previously observed when adding ammonium chloride 10 mM to the incubation medium.

As in the case of an artificial addition of ammonium chloride, said potentializing effect is obtained neither with ricin, nor with the chain A of ricin, nor with an immunotoxin non-specific of the studied cells.

In the conditions of this example, the cytotoxic activity of the anti T65 immunotoxin in the presence of the immunoenzymic conjugate used is about 130,000 times that of the chain of ricin and it is even about 11 times more powerful than that of ricin.

EXAMPLE 3

Immunoenzymic conjugate obtained by reacting an anti-DNP antibody substituted by a maleimide group and a urease of vegetable origin (a) Anti-DNP antibody This antibody is a monoclonal antibody which has been purified by the conventional techniques from abdominal dropsy fluid of mice of Balb/C strain in which the hybridoma $F_9$ has been transplanted.

Said hybridoma was itself obtained by fusion between splenic cells of mice of Balb/C strain immunized with bovine gamma-globulin on which have been priorly fixed 20 DNP radicals per mole with cells of the murin NS 1 myeloma stock, and isolated by cloning, according to the conventional techniques. The resulting antibody is an immunoglobulin of class G and of isotype 2b whose constant of affinity (measured for the ligand $\epsilon$-CNP-lysin) is $1,8 \times 10^8 M^{-1}$.

(b) Activated anti-DNP antibody

To 2.5 ml of a solution of anti-DNP antibodies (concentration 9.7 mg/ml in the phosphate 125 mM buffer, pH 7.0) are added 10 µl of dimethylformamide containing 0.4 mg of N-hydroxysuccinimide ester of m-maleimidobenzoic acid. The mixture is incubated for half-an-hour at 25° C. The solution is thereafter deposited on a Sephadex G25 column of 10 ml balanced in the phosphate 125 mM (7.0 pH) buffer. Elution is controlled by measuring the optical density at 280 nm. 2.5 ml are recovered from the exclusion volume of the column. The substitution rate is measured on an aliquot by reaction with an excess of $^{14}$C-cystein.

A solution is thus obtained of concentration 8 mg of antibodies per ml, with a substitution rate of 3.5 maleimide groups per mole of antibody.

(c) Urease

The enzyme used is the urease of SIGMA origin (type VII, ref. U 0376), assayed at 170 units per mg. One unit is the quantity of enzyme permitting the release of 1 micromole of $NH_4^+$ per minute at 20° C. and at pH 7.0, from urea.

This enzyme possesses naturally 27 thiol groups per mole of molecular weight 480,000. Said thiol groups, assayed by the ELLMAN method, are not all necessary to the enzymic activity. Some can therefore be used in the coupling with the activated antibody.

(d) Coupling of the antibody with the enzyme

Immediately after removing the salt on a G 25 column, 2.4 ml of the activated antibody solution are mixed with 2.0 ml of urease solution (concentration of 24 mg/ml) in the phosphate 125 mM buffer, pH 7.0. The mixture is incubated for 1 hour at 25° C. and deposited after centrifugation over a 450 ml Sephadex G200 gel column balance in the PBS buffer. Elution is controlled by measuring the optical density at 280 nm and by measuring the urease activity according to the SUMMER technique.

The fractions containing the strongest urease activities are re-grouped and thus 14 ml of conjugate solution (concentration 102 units per ml) are obtained.

If an aliquot fraction of this solution is chromatographed over a Protein A-Sepharose gel column, it is found that 30% of the urease activity are not left on the column. The rest of the urease activity is eluted at the same time as the antibody by the buffer of pH 3.5. A control experiment shows that the urease not coupled with the antibody is definitely not fixed by the column. This proves that 70% of the urease activity of the re-grouped fractions really belong to an antibody-urease conjugate. For the test described hereinafter, the contaminating free urease has not been removed from the solution, this urease being effectless in the conditions used, as described hereafter.

EXAMPLE 4

Potentialization of the anti T65 immunotoxin by the immunoenzymic conjugate of Example 3

The conjugate according to the invention, obtained as indicated hereinabove (Example 3) was tested with regard to its biological properties and in particular to its capacity to potentialize the activity of the anti-T65 immunotoxin in an appropriate cellular model.

Said model is constituted by cells from the lymphoblastoid human CEM cellular stock normally carrying the antigen T65. This antigen, against which is directed the immunotoxin used, constitutes the first target-antigen of the model. It is also possible to mark these cells with trinitrophenyl hapten (TNP) according to the technique described in Applicants' earlier appliction No. 78 27 838. Said hapten is perfectly recognized by the anti-DNP antibody contained in the tested immunoenzymic conjugate and therefore constitutes the second target-antigen of the model. It has been found that the marking of the cells by TNP hapten does not affect the viability of the cells nor the fixation of the anti-T65 immunotoxin on these cells.

The basic property of the immunotoxins being to inhibit the proteosynthesis of the target-cells, the test conducted consists in measuring the effect of the tested substances on the incorporation of $^{14}$C-leucine into the cancer cells in culture.

These measurements are carried out according to a technique adapted from the described in the Journal of Biological Chemistry, 1974, 249 (11), 3557–62 using the $^{14}$C-leucine tracer to determine the proteosynthesis rate. The determination of incorporated radioactivity is effected here on whole cells isolated by filtration.

It is possible from these determinations to plot dose/effect curves, the x-axis representing the molar concentration of chain A of the tested substances, and the Y-axis, the incorporation of $^{14}$C-leucine expressed as percentage of the incorporation of the control cells in the absence of any substance affecting the proteosynthesis.

For each substance studied, the concentration which inhibits 50% of the incorporation of $^{14}$C-leucine or "inhibitory concentration 50" (IC 50) may thus be determined.

The different tests of this experiment have been conducted as follows. The corresponding experimental results are given in FIG. 2.

(a) The control tests carried out in Example 2 (a) were not repeated since they can be considered as valid in the present example.

(b) CEM cells marked by TNP are incubated for 18 hours at 37° C. in the presence of an anti-T65 specificity immunotoxin obtained as indicated in Applicants' earlier application No. 81 21 836, and then subjected to the incorporation of the radioactive tracer. The cytotoxicity curve is identical to that obtained with the same cells, but not marked by TNP, in the same conditions of incubation, thereby proving that the marking of these cells by TNP is correctly effected (Curve 6).

(c) CEM cells marked by TNP are first incubated for one hour at 4° C. in the presence of non-conjugated urease in the proportion of 1 U/ml, then washed and incubated for 18 hours at 37° C. in the presence of anti-T65 immunotoxine in sole concentration of $10^{-9}$M and urea 5 mM, after which they are subjected to the incorporation of the radioactive tracer.

The $^{14}$C-leucine incorporation value obtained in this test (65%) is indistinguishable from that obtained with the same concentration of anti-T65 immunotoxin in test (b). This result proves that incubation in the presence of non-conjugated urease entails no bonding of the urease to the cells and consequently no potentialization of the anti-T65 immunotoxin effect.

(d) CEM cells marked by TNP are first incubated for one hour at 4° C. in the presence of the previously described immunoenzymic conjugate used at a concentration of 1.02 U/ml. It was also checked that this conjugate, when used in these conditions, has no inherent cytotoxicity on the cells used. The cells are then washed to eliminate any non-fixed conjugate, then they are incubated for 18 hours at 37° C. in the presence of anti-T65 immunotoxine and urea 5 mM. The cells are finally subjected to the incorporation of the radioactive tracer. The IC 50 thus obtained is $2,4 \times 10^{-13}$M. (Curve 7).

This value which is quite comparable to that obtained when using the conjugate of example 1, represents a remarkable potentializing effect of the immunoenzymic conjugate towards the immunotoxin.

This test proves that this potentializing effect indicates the fixation of the immunoenzymic conjugate on the antigen corresponding to its immunological specificity. Said fixation withstands the washing of the cells and leaves on the surface thereof some enzymically active urease which produces $NH_4^+$ ions from the urea present, in the incubation medium, with the immunotoxin, this resulting in the potentializing effect of the $NH_4^+$ ions.

The potentializing effect obtained is quite similar to that observed when the incubation takes place in the presence of ammonium chloride 10 mM added to the incubation medium instead of the immunoenzymic conjugate/substrate system.

Figure 2:
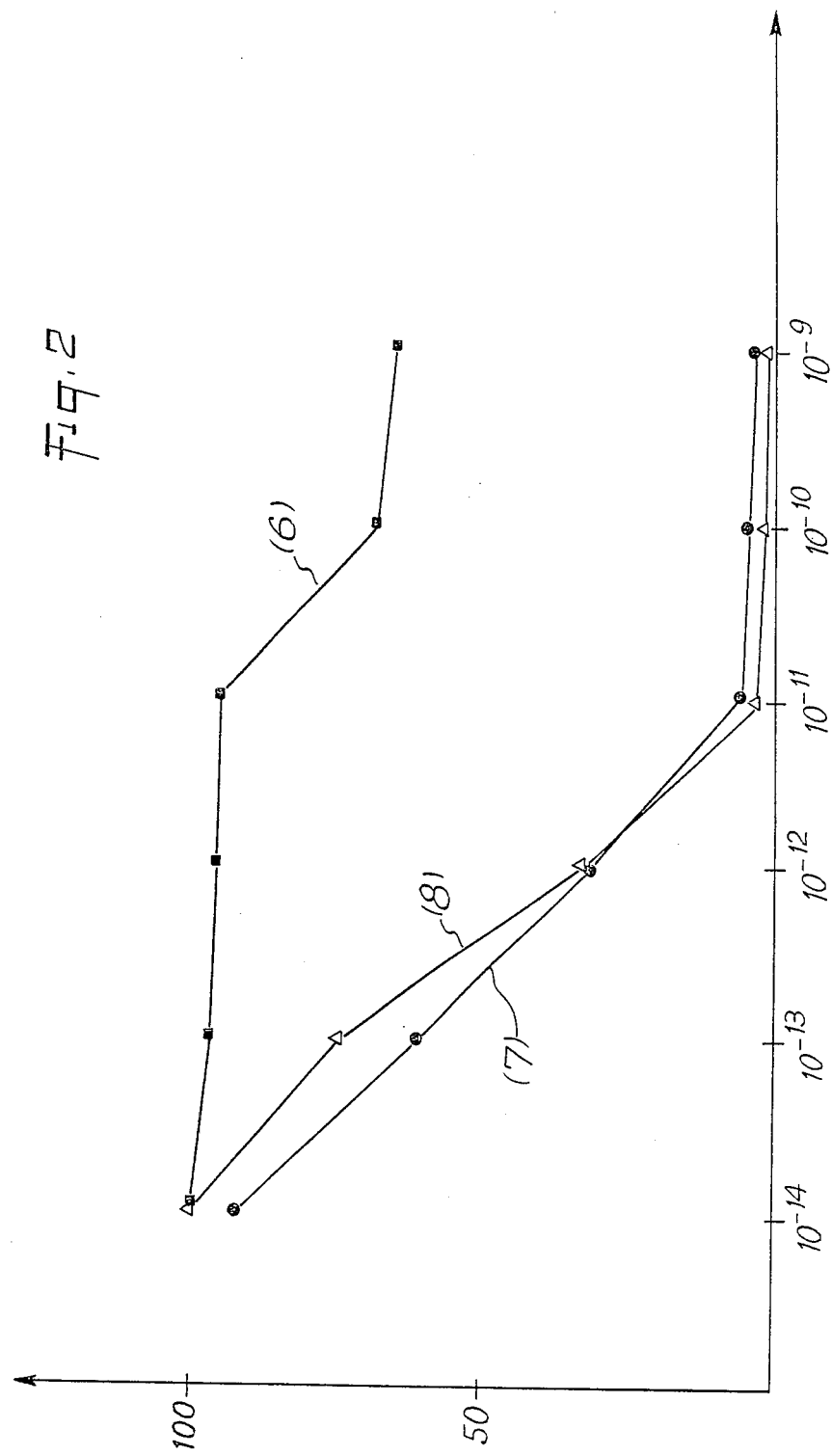

In the case where ammonium chloride is added, the IC 50 obtained is indeed $3,8 \times 10^{-13}$M as shown by the corresponding curve in FIG. 2 (Curve 8).

The foregoing examples show that the products according to the invention can be used in human therapeutics.

The new drugs according to the invention are presented in injectable form, for preferred administration by intraveinous route. They can be used for the treatment of any cancerous or non-cancerous disorders, responsive to the antibody used for preparing the immunotoxin. They are to be used in doses and conditions which will be determined in each case as a function of the patient and of the nature of the disorder.

What we claim is:

1. An immunoenzymic conjugate comprising an antibody or a fragment thereof having the capacity to recognize a specific antigen, covalently bonded to an enzyme capable of producing ammonium ions from natural substrates well tolerated in higher animal organisms.

2. A conjugate as claimed in claim 1 wherein the covalent bond is a disulfide bond.

3. A conjugate as claimed in claim 1, wherein the covalent bond is a thioether bond.

4. A conjugate as claimed in claim 1, wherein the enzyme covalently bonded to the antibody or fragment thereof, is selected from the group consisting of a sub-group 1–4 containing amino-acids-dehydrogenase and amino-oxydase, a sub-group 3–5 enzyme comprising the enzymes hydrolizing amines, amidines, and other C—N nonpeptidic bonds, a sub-group 4–2 and 4–3 enzyme catalyzing degradation reactions with formation of non-saturated compounds.

5. A conjugate as claimed in claims 4 wherein the enzyme covalently bonded to the antibody or a fragment thereof, is 1-4-1-1:alanine dehydrogenase, 1-4-1-3:glutamate dehydrogenase NAD (P)+, 1-4-1-5:L-amino-acids dehydrogenase, 1-4-3-2:L-amino-acids oxydase, 3-5-1-1:asparaginase, 3-5-1-2:glutaminase, 3-5-1-4:amidase, adenosine deaminase, 3-5-4-66:adenosine monophosphate deaminase, 3-5-4-21:creatinine deaminase, 4-2-1-13:L-serine dehydratase, 4-2-1-16:L-threomine dehydratase, 4-3-1-1:aspartate-ammonia-lyase, 4-3-1-3:histidine-ammonia-lyase or 4-3-1-5:phenylalanine-ammonia-lyase.

6. A conjugate as claimed in claim 5 wherein the covalent bond is a disulfide bond.

7. A conjugate as claimed in claim 5 wherein the covalent bond is a thioether bond.

8. A pharmaceutical composition comprising a therapeutically effective amount of at least one immunotoxin formed between the A chain of ricin and an antibody or an antibody fragment and a potentiating amount of at least one immunoenzymic conjugate as claimed in claim 1, and an pharmaceutically acceptable carrier.

9. A pharmaceutical composition as claimed in claim 8 in injectible form.

10. A method of potentiating an immunotoxin formed between the A-chain of ricin and an antibody or an antibody fragment, at the immediate environment of a mammalian target-cell for said immunotoxin, which comprises administering a potentiating effective amount of the immunoenzymic conjugate of claim 1 to a patient having target-cells, to cause reaction of said immunoenzymic conjugate with a natural substrate located in the area of the target-cells to generate a potentiating amount of ammonium ions for said immunotoxin.

11. A method of potentiating an immunotoxin formed between the A-chain of ricin and an antibody or an antibody fragment; at the immediate environment of a mammalian target-cell for said immunotoxin, which comprises administering a potentiating effecting amount of the immunoenzymic conjugate of claim 1 to a patient having target-cells for said immunotoxin, and wherein a substrate for the enzyme of the immunoenzyme conjugate is not present in the blood and the extra cellular liquid in a high enough concentration to effect a potentiating reaction between the substrate and the immunoenzymic conjugate, and administering an effective amount of a substrate to the patient being treated with the immunotoxin and immunoenzymic conjugate to cause reaction of said immunoenzymic conjugate with the substrate located in the area of the target-cells to generate a potentiating amount of ammonium ions for said immunotoxin.

* * * * *